United States Patent [19]

Kemeny et al.

[11] Patent Number: 4,883,963
[45] Date of Patent: Nov. 28, 1989

[54] OPTICAL ANALYSIS METHOD AND APPARATUS HAVING PROGRAMMABLE RAPID RANDOM WAVELENGTH ACCESS

[75] Inventors: Gabor J. Kemeny; David L. Wetzel, both of Manhattan, Kans.

[73] Assignee: Bran+Luebbe GmbH, Norderstedt, Fed. Rep. of Germany

[21] Appl. No.: 856,289

[22] Filed: Apr. 28, 1986

[51] Int. Cl.$^4$ .......................... G01J 3/42; G01N 21/35
[52] U.S. Cl. .................................... 250/339; 250/343; 350/358; 350/372; 356/308; 356/326
[58] Field of Search ........................ 250/373, 339, 343; 350/358, 372; 356/308, 309, 326, 328, 332, 331

[56] References Cited

U.S. PATENT DOCUMENTS

| | | | |
|---|---|---|---|
| 3,520,614 | 7/1970 | Goldstein | 356/320 |
| 3,679,288 | 7/1972 | Harris | 350/358 |
| 3,828,173 | 8/1974 | Knepler | 235/151.35 |
| 3,861,788 | 1/1975 | Webster | 350/315 |
| 3,944,334 | 3/1976 | Yano et al. | 350/372 |
| 3,944,335 | 3/1976 | Saito et al. | 350/372 |
| 3,953,107 | 4/1976 | Yano et al. | 350/358 |
| 4,052,121 | 10/1977 | Chang | 350/358 |
| 4,082,464 | 4/1978 | Johnson | 356/188 |
| 4,236,076 | 11/1980 | Judge et al. | 250/347 |
| 4,264,205 | 4/1981 | Landa | 356/326 |
| 4,285,596 | 8/1981 | Landa | 356/308 |
| 4,286,327 | 9/1981 | Rosenthal et al. | 364/498 |
| 4,342,502 | 8/1982 | Chang | 350/358 |
| 4,404,642 | 9/1983 | Rosenthal | 364/571 |
| 4,540,282 | 9/1985 | Landa et al. | 356/328 |
| 4,602,342 | 7/1986 | Gottlieb et al. | 356/372 |
| 4,663,961 | 5/1987 | Nelson et al. | 73/24 |

OTHER PUBLICATIONS

Harris et al., "Acousto—Optic Tunable Filter", Journal of the Optical Society of America, vol. 59, No. 6, (Jun. 1969), pp. 744–747.
Chang, "Non Collinear Acousto—Optic Filter with Large Angular A perfume", Applied Physics Letters, vol. 25, No. 7, (10/1977), pp. 370–372.
Wetzel, "Near—Infrared Reflectance Analysis", Analytical Chemistry, vol. 55, No. 12, (10/1983), pp. 1165A–1171A.
Jacob et al., "Development of an AOTF Spectrometer", SPIE, vol. 22, pp. 40–46.

Primary Examiner—F. L. Evans
Attorney, Agent, or Firm—Rodman & Rodman

[57] ABSTRACT

The optical reflectance or transmittance concentration analyzer includes an acousto-optical tunable filter (AOTF). The AOTF is tuned by a computer controlled digital-to-analog converter through a tunable sweep oscillator. Tuned beams can be selected according to their direction of propagation or according to their polarization behavior. Therefore, if desired, a pair of crossed polarizers can be used to select one of the tuned monochomatic light beams that pass from a light source through the AOTF. To obtain rapid wavelength change along with electronic chopping or wavelength modulation, the digital-to-analog converter output is combined with the output of a high speed signal generator. The modulated light is conducted directly or through a fiber optic cable to the location of the optical measurement and impinges upon the sample where it is reflected or transmitted. The emerging light is collected onto detector(s). The measurement time interval can be distributed among the required wavelengths or wavelength pairs according to an unequal scheme to decrease the error of the result in a calibration equation. The apparatus is particularly adaptable for use as an on-line concentration monitor in industrial process control because of its stability, efficiency and ability to perform quick analyses.

17 Claims, 9 Drawing Sheets

A. Tuned extraordinary light
B. 0th light (transmitted)
C. Tuned ordinary light

OPTICAL ANALYSIS METHOD AND APPARATUS HAVING PROGRAMMABLE RAPID RANDOM WAVELENGTH ACCESS

BACKGROUND OF THE INVENTION

The invention relates to optical analyzing instruments, more particularly to reflective or transmissive optical analyzing instruments with the purpose of determining the composition of solid, liquid, slurry or paste samples by their near-infrared, infrared or visible absorbances with special respect to industrial on-line monitoring applications.

The background of the invention is the empirical correlation near-infrared reflectance analysis method first suggested and elaborated by Karl H. Norris of the USDA, Beltsville, Md., in the mid-sixties. It was observed, that if different wavelength near-infrared radiation is incident on the surface of the sample it is absorbed or reflected to certain extents, depending on the characteristics, and thus the concentrations of the constituents of the sample. The reflected radiation can be collected by suitable optics and the radiation can be measured by a suitable detector arrangement. The concentrations of the material to be measured can be calculated from the intensities measured at different wavelengths. For a more detailed history and background see the article by David L. Wetzel published in Analytical Chemistry Vol. 55, p. 1165A (1983).

For the above purposes, in the past various instruments comprising different monochromators have been reported. Most systems were aimed at laboratory analysis of samples and it is difficult to apply the instrumental principles and systems in the prior art for industrial on-line concentration monitoring. Typically in on-line monitoring the samples are moving, in many cases they are inhomogeneous, thus to achieve the monitoring goals a large number of measurement should be done in a very short time, and the results averaged to reduce errors. In addition to the averaging requirement it would be needed to correct for the rapid changing of the sample, and possibly use optical data that were taken from the same part of the sample, in the calibration equation. This can be achieved in principle by applying a "stopped-flow" sampling, but this procedure is less representative to the bulk of the sample and also much too slow for most control purposes.

In the prior art interference filter systems with a perpendicular direction of light beam are described in U.S. Pat. Nos. 3,828,173 and 4,236,076. In both systems discrete wavelength interference filters are mounted in a turret, thus the rate of the wavelength selection is limited by the mechanical means to rotate the turret.

A special mention among interference filter instruments is deserved for a system in the prior art, described in U.S. Pat. Nos. 4,286,327 and 4,404,642. As light sources infrared emitting diodes (IREDs) are used, whereas all other instruments in the prior art utilize wide wavelength band quartz tungsten-halogen light sources. The advantage of the special light source is that it dissipates only a fraction of what conventional light sources do, and can be activated very rapidly by a timer through a microcomputer. In return for these advantages the wavelength region is constrained to the region of the IREDs (about 850-1050 nm). In this region a very sensitive Si detector can be used but only a few chemical components show characteristic absorbances.

Tilting interference filter systems are described in U.S. Pat. Nos. 3,861,788 and 4,082,464. The interference filters are mounted on paddle wheels, and rotated to result in a wavelength shift as the angle of the filter and the incident beam varies in time. These systems produce continuous wavelength change, but only very small fractions of the whole rotation can be considered "useful" time, when the filter is exactly producing the required wavelengths. There is also considerable dead time, when the beam is mechanically blocked between filters.

Diffraction grating systems for optically analyzing samples have been described in the prior art. Vibrating holographic grating systems, capable of up to ten scans per second were presented in U.S. Pat. Nos. 4,264,205, 4,285,596 and recently in U.S. Pat. No. 4,540,282. The vibrating grating principle allows only sequential access to the individual wavelengths as the whole spectrum is swept through in time. One of the disadvantages in the high speed applications of grating monochromator is that the signal-to-noise ratio cannot be enhanced by chopping and narrow noise bandwidth phase sensitive (lock-in) amplification. This technique can only be applied in slow point-to-point scan grating systems, where the grating is stopped at every required wavelength, and enough light chopping periods are allowed to elapse for the signal intensity to be precisely measured. Thus the total spectrum measurement time is increased up to about a minute.

Another trade-off in mechanical (rotating sector) chopper systems is, that only half of the measurement time is spent by the detector collecting light at the required wavelenth, in the other half of the period a fast dark compensation occurs, carrying no "wavelength information". Lock-in amplification is described in U.S. Pat. No. 4,236,076, where the light is modulated by chopping the light, periodically referencing by a tilting mirror and changing the wavelength by changing interference filters in the beam. A disadvantage of this system for the monitoring of rapidly changing material is that the wavelength change is the slowest of the mentioned three modulation, the rate being several seconds between consecutive wavelength choices.

Figure 1:
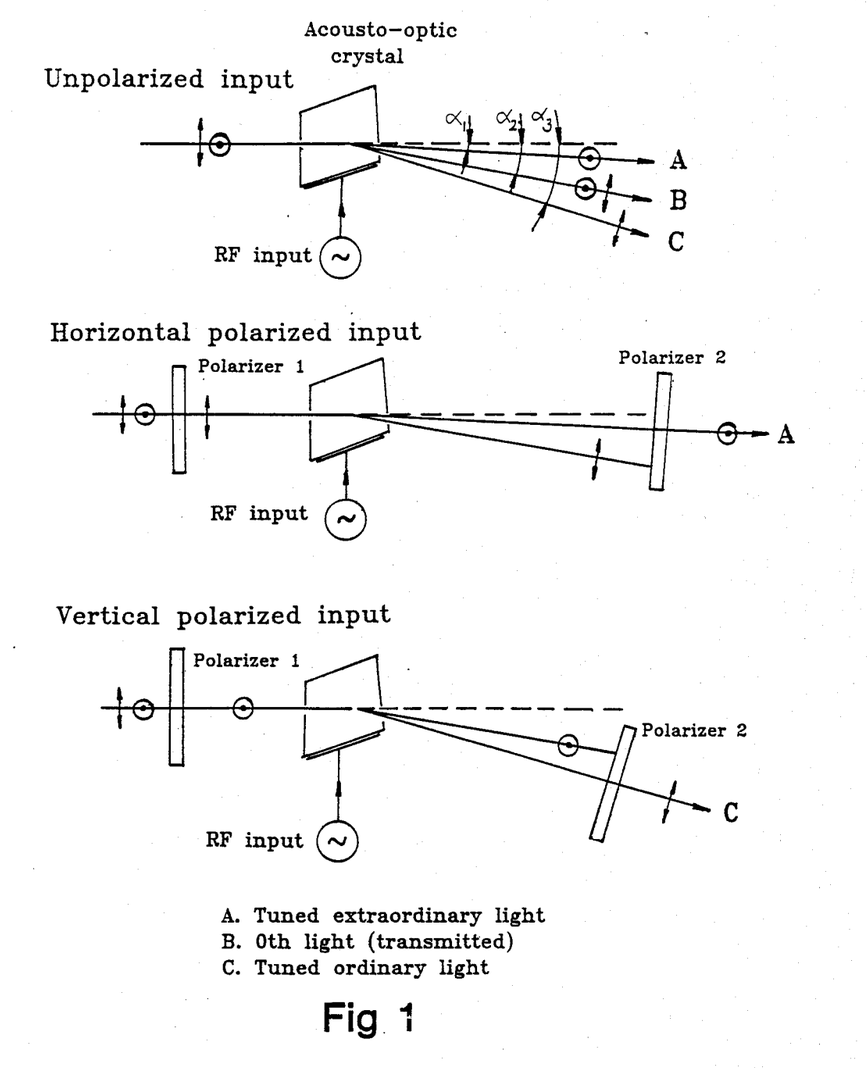
FIG. 1. Polarization characteristics of acousto-optic tunable filter.

The further increase of the speed, improvement of the efficiency of the monochromator and the analyzer system runs into serious problems with the mechanical monochromatic systems in the prior art. From among the non-mechanically tunable optical devices acousto-optical tunable filters (AOTF) have been described by S. E. Harris and R. W. Wallace in the Journal of the Optical Society of America, Vol. 59, pp. 744-747 (1969). This early model was tunable from 400 nm to 700 nm by applying 428-990 MHz acoustic frequency via an acoustic transducer layer attached to a LiNbO crystal. Since then various acousto-optic devices have been described by I. C. Chang in Applied Physics Letters Vol. 25, pp. 370-372 (1974) and also in U.S. Pat. Nos. 3,679,288; 3,944,334; 3,944,335; 3,953,107; 4,052,121 and 4,342,502. In the above mentioned disclosures the geometry, the material of the crystal used and the optical arrangement varies, but in common all acousto-optic tunable filters utilize the principle that the direction of propagation and the direction of polarization of an appropriate incident ray is changed by the application of a high frequency optical modulation of the crystal. The different frequencies give rise to different densities of index of refraction fronts due to local stresses caused by the acoustic waves. This tuning can be activated over a relatively wide frequency(-wavelength) range, thus rendering the device ideal for optical tuning purposes. If the wideband input light is polarized, another polarizer (the so called analyzer) can select the tuned monochromatic ray from the traversing untuned polychromatic light. FIG. 1 shows a possible optical arrangement of an AOTF commercially available. Since the wavelength accessibility is influenced by the size and geometry of the acousto-optic crystal and the velocity of the sound travelling in the crystal, a 100–100,000 fold advantage in the speed of the wavelength change rate may be obtained compared to other analyzers in the prior art.

SUMMARY OF THE INVENTION

The present invention is an improvement over prior optical reflectance or trasmittance analyzers. The improvements make the analyzer faster, more efficient, more stable and mechanically less complicated, thus also smaller and lighter. The above characteristics render the instrument able to be used as an on-line concentration monitor in industrial process control.

The object of this invention is to improve the speed of the wavelength change to increase scan rate for better averaging of moving or changing samples. The samples are moving under process conditions, where solid or liquid material is being transported via tubes, chutes, conveyor belts and similar devices.

Another objective of the present invention is to improve the efficiency of the near-infrared optical analysis by proposing a measurement scheme, where the unused optical instrument time is minimized.

Yet another objective is to reduce the thermal and vibration sensitivity of the presently known optical analyzers, especially bearing in mind the industrial and process conditions, where most of these proposed instruments would be installed.

One of the basic recognitions in the present invention is that the increase of the wavelength selection rate has serious limitations if pursued in a mechanical manner. It was therefore established, that one of the electro-optical, electromagneto-optical or acousto-optical tunable devices have to be included in a new optical system to achieve shorter wavelength access time. On the basis of the wavelength range and tunability the AOTF was singled out to be incorporated in a new system.

Figure 2:
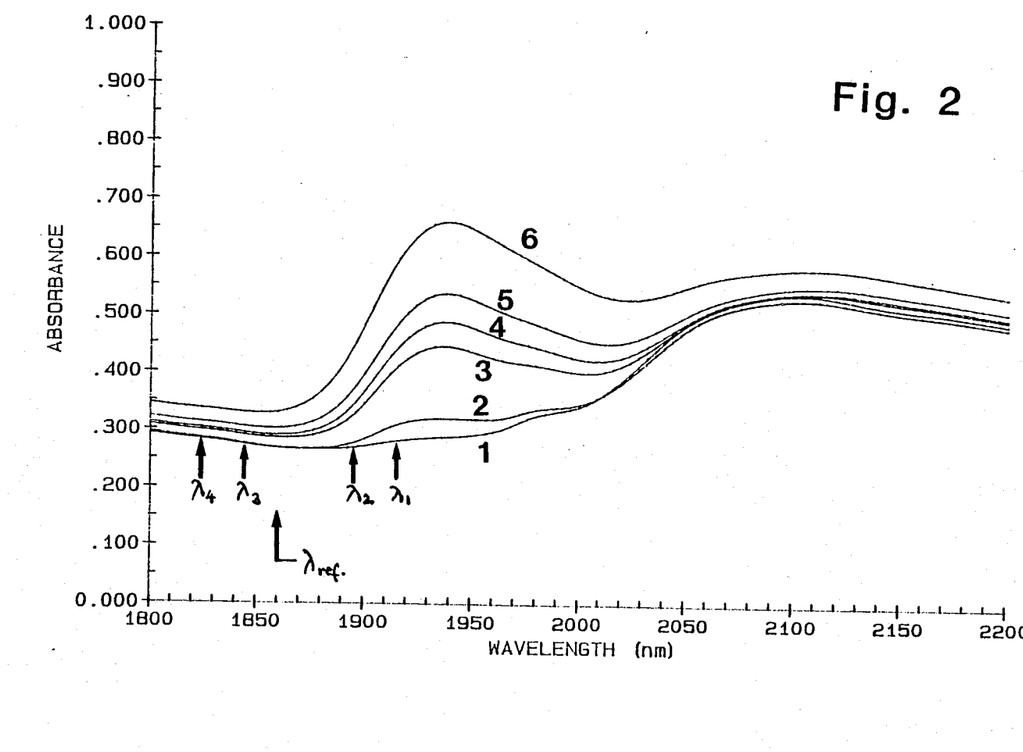
FIG. 2. Near-infrared spectral portion of wheat samples with different (increasing) moisture content.

FIG. 2 shows a portion of the near-infrared reflectance spectra of six ground wheat samples with increasing different moisture contents. As it can be seen, this constituent can be quantitated by measuring the height of the peak around 1940 nm. To correct for the baseline changes, most pronounced on spectrum 6, for example a reference wavelength ($\lambda_{ref}$) be used. The other option is to use the difference spectrum (the extreme case being the derivative of the spectrum), which will not contain the baseline shifts, originating from particle size differences, background radiation or other effects, only the steeper spectral changes. Thus the differences between the intensities between $\lambda_1$ and $\lambda_2$ also characterize the amount of moisture in the sample. Another or a plurality of differences ($\lambda_3$, $\lambda_4$ etc.) can be included in the calibration equation.

It has to be realized that the optimal wavelengths and wavelength combinations vary from application to application, thus in a general purpose instrument it is very desirable to be able to access all wavelengths in any random manner.

Thus it was further recognized that random wavelength access is desirable and possible with an AOTF while avoiding the unnecessary dead times typically associated with rotating or tilting filters or the serial wavelength accessibility typical of the grating monochromator systems.

It was also recognized that along with the computer controlled electronic wavelength selection, the necessary chopping or wavelength modulation can also be carried out without any moving parts, thus significantly simplifying the construction of such an optical analysis instrument.

Figure 3:
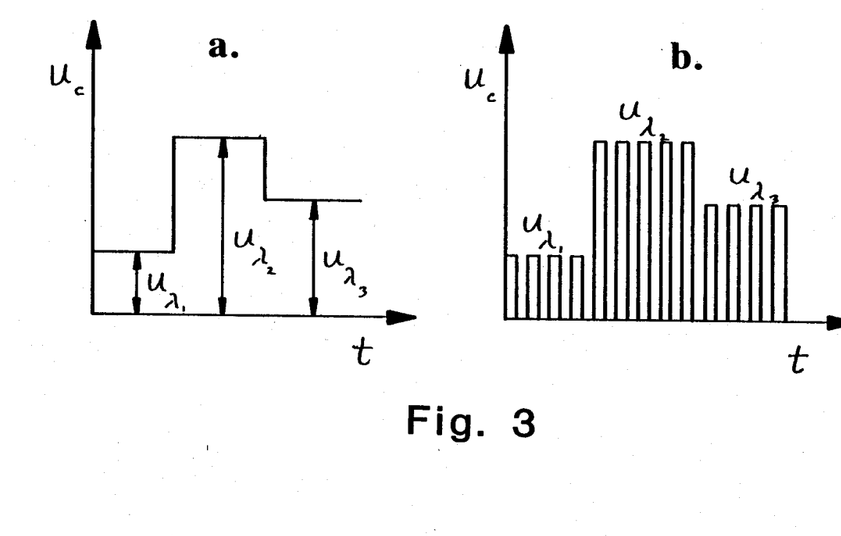
FIG. 3. Tuning control schemes for the tunable sweep oscillator

FIG. 3 shows two typical tuning schemes, made possible by the present invention. Chart a. pesents the selection of different wavelengths via applying different control input voltages ($U_c$) to the tunable sweep oscillator. In this scheme either there is no lock-in amplification or only a mechanical chopping, which should be faster than the wavelength change. On the other hand chart b. shows a control scheme with rapid on-off tuning of the sweep oscillator. Beside selecting $\lambda_1$, $\lambda_2$ or $\lambda_3$ (by selecting $U_c$ control voltages) the rapid on-off provides electronic chopping, and does that only on the selected wavelength. With a phase sensitive detection (lock-in amplification) the preferred selected wavelength information is only amplified and all other background signal and noise of other frequencies are suppressed. With this chopping scheme the frequency is controlled electronically and thus is kept very precise as opposed to the frequency error experienced with mechanical chopping devices. The bandwidth of the amplification therefore is much narrower, reducing the noise of the apparatus. The noise can further be decreased by the usage of a narrow bandpass prefilter or other electronic means.

Figure 4:
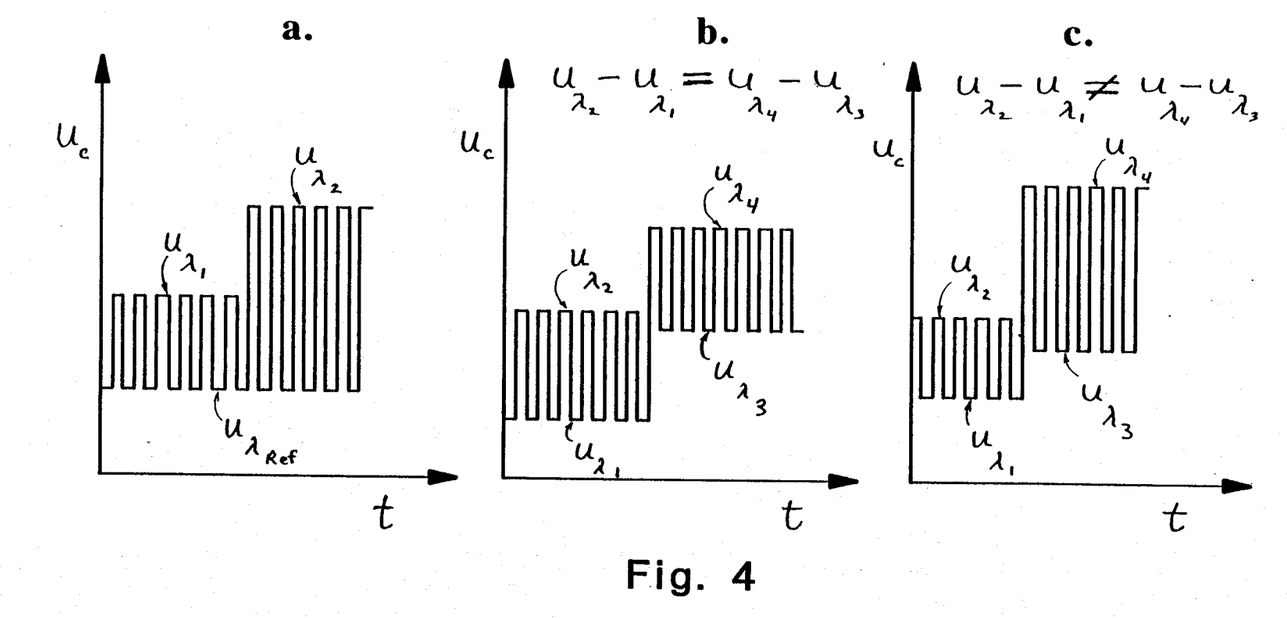
FIG. 4. Differential tuning schemes for the tunable sweep oscillator input.

Yet further it was recognized in the present invention that with the previous "on-off" chopping mode every second half cycle time carries no wavelength characteristic information. When the radiation is blocked, the signal is only used to correct for the background. With a fast tunable device, like with the proposed AOTF wavelength modulation is also possible, wherein the radiation is not blocked in every half cycle, rather the signal intensity is measured at an alternative wavelength. The frequency of this wavelength modulation is used as a reference for a phase sensitive amplification. Three possible tuning schemes are shown on FIG. 4. FIG. 4/a shows $\lambda_1-\lambda_{ref}-\lambda_1-\lambda_{ref}\ldots\lambda_2-\lambda_{ref}-\lambda_2-\lambda_{ref}$ sequences, where $\lambda_{ref}$ is constant throughout the whole experiment. $\lambda_i-\lambda_{ref}$ sequence is repeated as many times as required by the output of the lock-in amplifier (LIA) to be settled (typically 10–12 cycles) and sampled by the analog-to-digital converter (ADC), connected to the output of the lock-in amplifier. The lock-in amplifier usually has very narrow bandpass characteristics, but optionally the signal-to-noise ratio (SNR) can further be enhanced by inserting a narrow band preamplifier at the input of the lock-in amplifier.

First derivative (first difference) spectrum modulation scheme is shown on FIG. 4/b. The difference of the consecutive wavelenth pairs is kept constant ($\lambda_2-\lambda_1=\lambda_4-\lambda_3$), and similarly each pair is repeated as long as one measurement point can be taken and recorded via the lock-in amplifier and the ADC. It is also recognized that this tuning can be carried out by initiating the change of the base wavelength selection ($\lambda_1$ and $\lambda_3$) by a computer controlled digital-to-analog converter (DAC) via the tunable sweep oscillator, whereas the chopping modulation is favorable originating from a signal generator circuit, providing a constant periodic signal during the whole measurement. This latter signal is simply added to the aforementioned base signal, the total control signal ($U_c$) being shown in FIG. 4/b.

If only a few wavelengths are used for the analytical purposes they can also be randomly selected by the computer control, as shown in FIG. 4/c. The tuning difference is not kept constant in this scheme.

Furthermore it is also recognized that complex optical instruments containing numerous moving parts are more susceptible to failure, more sensitive to vibration and to changing thermal conditions. In addition, the instruments in the prior art containing interference filters are sensitive to thermal changes, resulting in a shift of the peak transmittance wavelength with different temperatures. As a result of the simple optical layout and the nature of the wavelength selection of the AOTFs according to the present invention are insensitive to vibrations or to ambient temperature changes except to sudden temperature shocks.

The objects of the invention are achieved by a system comprising an AOTF. The light emerging from a wide band source, e.g. a quartz tungsten-halogen lamp is collimated and polarized by a suitable polarizer. Relatively inexpensive sheet type polarizers are available, however the their extinction ratio is not uniformly good throughout the entire visible or near-infrared spectrum. Glan-Thompson or Glan-Taylor type polarizers develop an extiction ratio better than $10^{-5}$, thereby suppressing the nonmodulated light much better, bur they are more expensive. The input and output beams are collinear as in the case o the sheet polarizers. Wollaston prism type polarizers are also potentially useful because of their good extinction ratio, but the input and output beams are not collinear, and the angle deviation has to be considered in the optical design.

With crossed polarizers placed in front of the AOTF and behind it, only the tuned ordinary or the tuned extraordinary beam is selected and the unmodulated traversing light is diverted or absorbed by the second polarizer. As the input polarization direction either vertical or horizontal direction can be chosen, the selection determines, which of the output beams can be used. The AOTF is driven by a sweep oscillator, which provides the necessary input for the acoustic transducer mounted on the crystal For easy control interfacing the voltage tuned sweep oscillators are advantageous. Any of the tuning schemes of FIGS. 3 and 4. can be used, however scheme of FIG. 4/b. is easily implemented up to very high speeds without sophisticated computer hardware or software. A separate signal generator provides the high frequency (up to 100 kHz) square-wave or sinewave signal that is added to the much slower changing base wavelength selection signal (0–10 kHz) generated by the DAC circuit, controlled by a microcomputer.

The reference signal from the signal generator circuit serves as an input for the narrow band phase sensitive amplifier (LIA). It is good practice to let about 10–12 cycle time elapse for the LIA output to settle. The output is filtred, and introduced into a computer controlled ADC. The rate of data acquisition is the rate of the base wavelength change, therefore it can be about 10–12 times slower than the highest speed event, the primary periodic wavelength modulation.

It was also recognized that in order to utilize the advantages of a high speed system, the choice of detectors should be based on their speed along with their sensitivity, noise equivalent power (NEP) and wavelength range. In contrast to most other optical analyzers in the prior art, where Si or PbS detectors were used, the apparatus according to the present invention along with Si,PbS,PbSe detectors may comprise Ge or cooled Ge detectors to match the speed of the AOTF and yet retain a wide enough wavelength range.

A further recognition is that fiber optic light transmission can very advantageously be applied in conjunction with the AOTF. Optical fibers are small diameter light conducting materials, with a small light input diameter and a limited light acceptance cone. In order to couple light into optical fibers it has to be focused onto the end of the small fiber, with no more, than the cone of acceptance. The non-distorted, collimated (and modulated) light emerging from the AOTF is ideally suited for focusing with the above requirements, with the help of a simple aspheric lens or an off-axis parabolic mirror.

The fiber optic transmission of the light from the monochromator, in this case from the AOTF to the optical head, where the light comes in contact with the sample is advantageous as only some minor electronic and optical components have to be exposed to the process environment, and the light source, monochromator, and most related electronics and computing means can be located elsewhere. The optical head serves for the illumination of the sample, but also to collect the radiation emerging from the sample. If the sample is solid, the diffusely transmitted or reflected light cannot be gathered with sufficient efficiency back into another fiber. Thus two different optical approaches have to be pursued. For clear liquids, where the transmitted light may return to the main optical/electronic unit for detection via a second optical fiber, thus isolating the optical head electrically. This feature may be very advantageous in the determination of concentrations in explosive or otherwise hostile environments.

If the sample is diffusely scattering the light it has to be collected by an integrating sphere or a suitable mirror directly onto a (larger surface) detector. In this case the optical head contains the collection optics, the detector(s) and the detector related electronics.

The result of the optical analysis is calculated by substituting the measured light intensity values into optimal calibration equations. It has to be realized, that the error of the analysis depends on the error of the individual optical measurement and on the magnitude of the constant with wich it is multiplied. These errors contributed to the individual terms are shown in equation 1.

$$Y[\%] = K_0 + K_1(I_1 + \epsilon_1) + K_2(I_2 + \epsilon_2) + K_3(I_3 + \epsilon_3) \qquad (1)$$

where Y is the chemical constituent to be measured, $K_0$ through $K_3$ are constants, $I_i$ is the signal intensity at wavelength $\lambda_i$, $\epsilon_i$ is the error at $\lambda_i$. In order to reduce the total measurement error the sum of the products $K_i\epsilon_i$ has to be decreased. With the computer controlled electronic tuning this error can be decreased by allowing different measurement times and number of averages for the different wavelengths. It is known that by increasing the measurement time or the number of averages by N, the signal-to-noise ratio can be increased by N. Because in a certain calibration equation the given errors are multiplied by widely varying constants it is very important to decrease the error at that wavelength where said K constant is large. Although it is cumbersome to derive an analytical equation for the best division of time between the various wavelengths mainly because of the square root function of the error reduction, it can be seen that for every error-constant distribution there is an optimum time distribution, other than not the equal sharing of measurement time. In general the longer time has to be spent thus the error decreased at wavelengths with larger constant multipliers, up to a certain point, where some other error terms start increasing at the remaining wavelengths with the shrinking time, compromising even the terms with smaller constants.

BRIEF DESCRIPTION OF THE DRAWINGS

FIG. 7b is an alternate embodiment of FIG. 7a.

DESCRIPTION OF PREFERRED EMBODIMENTS

Figure 5:
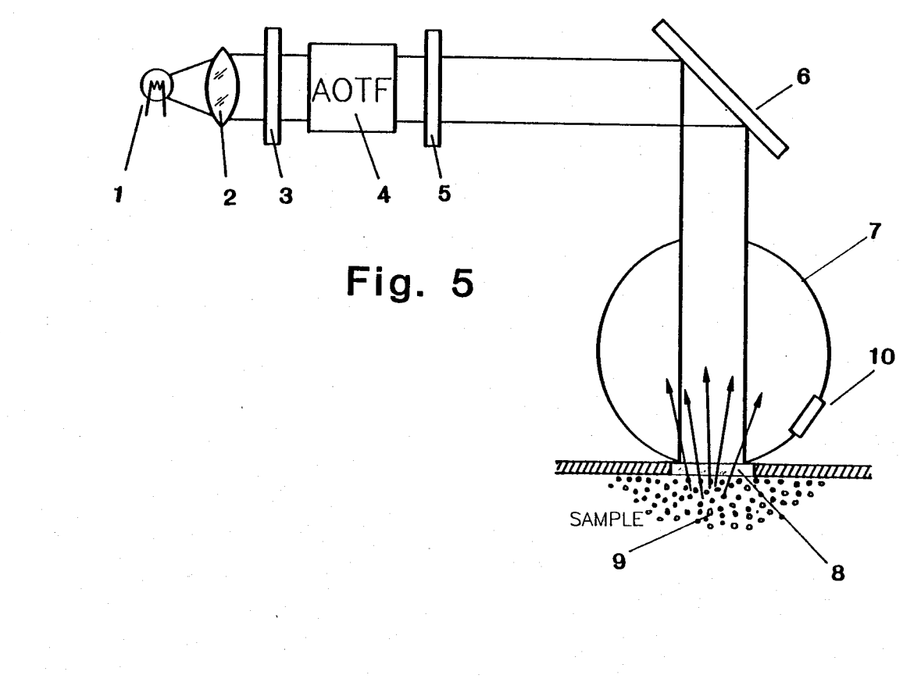
FIG. 5. Optical path and basic components of the apparatus of the invention.

In FIG. 5 the optical path of one of the preferred embodiments is shown, wherein light source 1 is an incandescent wide wavelength band quartz tungsten-halogen lamp. The light emerging from light source 1 is collimated by collimating lens 2. The preferred embodiment is not limited to lens type collimating devices. Collimating mirrors, preferably off-axis parabolic mirrors can also be used. The collimated light traverses through polarizer 3, which selects one of the polarization components, and either absorbs, reflects or directs the other component elsewhere. The collimated and polarized light enters the acousto-optic tunable filter (AOTF) 4. This latter device is arranged in a position and angle as it can best accept the polarized input light for consequent modulation. Modulated monochromatic and unmodulated light emerges from the AOTF 4. The unmodulated component retains its angle of polarization, whereas the modulated component, the light with the selected wavelength alters its direction of polarization by 90. Polarizer 5 is in a crossed position relative to polarizer 3, thus only the selected, modulated light component traverses through polarizer 5. The polarizers can be of any type that is effective in the selected wavelength region. Independent of the model of the polarizer, the second polarizer 5 should be arranged to take the expected small angle deviation of the emerging tuned beam into consideration. The sheet polarizer for example should be arranged to be perpendicular to this emerging tuned beam. The angle deviation, depending on the arrangement of the AOTF crystal and the choice of the ordiary or the extraordinary beam may vary from 1 to 10 this small angle is not shown on FIG. 5. The selected modulated wavelength beam is directed onto the surface of the sample. In one preferred embodiment this is done by mirror 6, through optical window 8. The sample 9 in this case solid material is placed near the opening of integrating sphere 7. The light impinging upon the sample is partly reflected and in part penetrating the sample where it suffers scattering, reflection and absorption. As a result light emerges from sample 9 back into integrating sphere 7. The light encounters multiple reflections and eventually falls onto the surface of detector 10.

Detector 10 can be either or more of the following types: Si,PbS,PbSe,Ge or cooled Ge to enhance the long wavelength limit of this type of detector.

Figure 6:
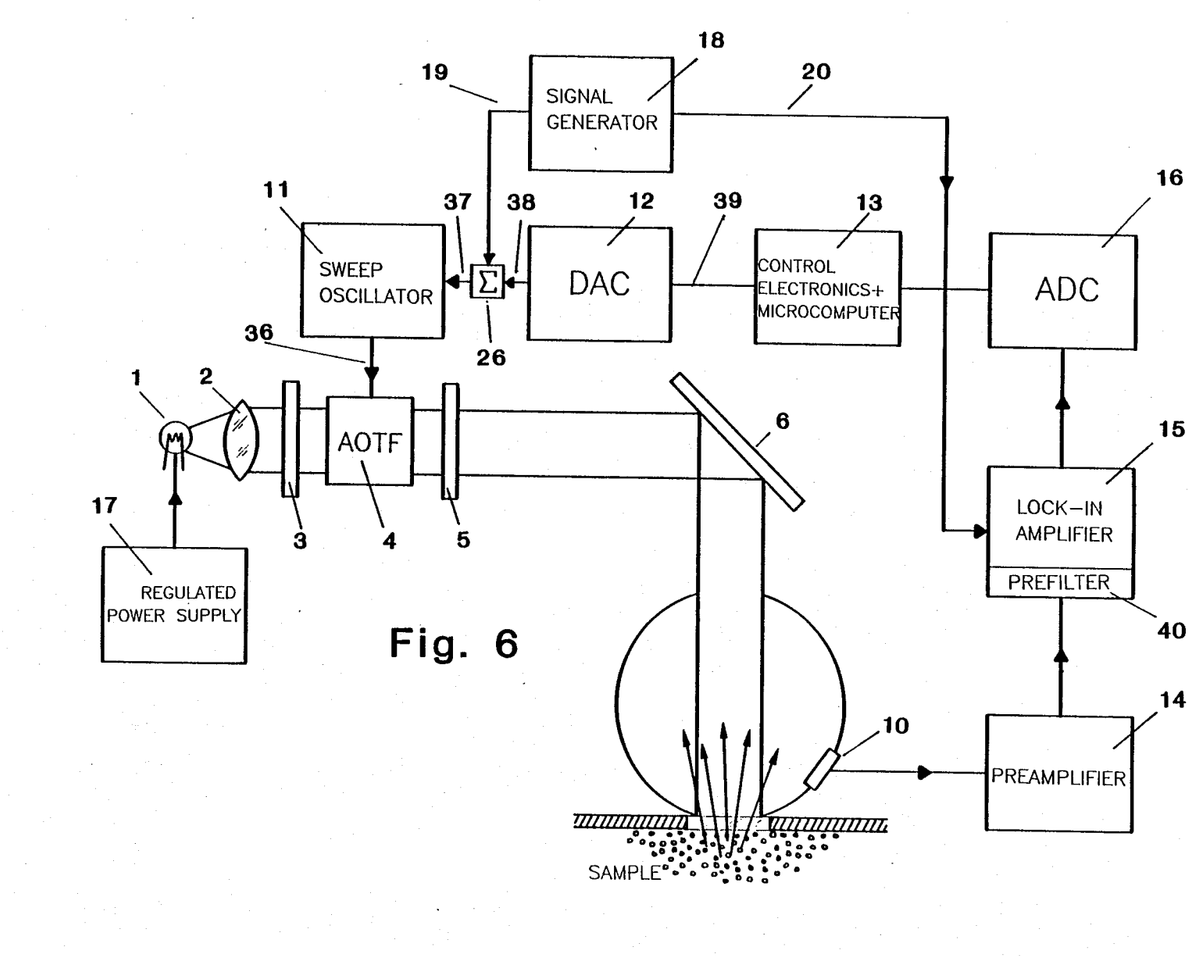
FIG. 6. Electronic block diagram of the apparatus of the invention.

FIG. 6. shows the block diagram of the related electronics of the preferred embodiment. Sweep oscillator 11 is connected to the AOTF 4 preferably via a short coaxial cable 36. Sweep oscillator 11 generates the RF signal necessary to drive the acoustic transducer located on one side of the acousto-optic crystal. Depending on the design of the crystal and the required wavelength range the acoustic frequency is several MHz to several hundred MHz. The output power at an adjusted impedance, to be coupled into the crystal should be enough to drive the crystal into saturation and provide maximum modulation efficiency. In this preferred embodiment sweep oscillator 11 is tuned to different output frequencies by a high impedance analog input. This analog control input 37 can be provided by preset or controlled analog voltage source. In this embodiment controlled voltage analog output 38 is ensured by digital-to-analog converter (DAC) 12, which is in turn driven by a microcomputer controller 13 through a standard computer communication line 39. Signal from detector 10 is introduced into preamplifier 14, the output of preamplifier 14 is connected to the signal input of lock-in amplifier (LIA) 15. An optional prefilter 40 may enhance the signal of known modulation frequency to suppress random noise of other frequencies. LIA 15 can generate its own reference signal by forming the amplified detector signal itself. External reference signal 20 is provided and connected to the reference input of the LIA 15.

Signal generator circuit 18 generates sinusoidal or rectangular output, which is connected to summation circuit 21, and a corresponding reference signal 20. Signals 19 and 38 will be added to provide combined output 37 for wavelength selection and wavelength modulation respectively. Regulated power supply 17 is connected to light source 1 to provide constant, noise-free light flux.

In one specific example of the preferred embodiment light source is a 50 W tungsten-halogen lamp driven by 5 V DC, collimating lens is f=17 mm aspheric lens (Melles Griot, Irvine, Calif.). The pair of polarizers are model 27360 iodine dyed polyvinyl-alcohol type sheet polarizers for the near-infrared region (Oriel Corp. Stratford, Conn.). The acousto-optic tunable filter is model EFL-F20R3A (Matsushita Electronic Components Co., Kadoma, Japan), with an optical aperture of 7×7 mm. The optical tuning range is 1.4–2.5 um, with a deflection efficiency better than 70%. The fastest wavelength access time is 11 us, the optical resolution varies as a function of scan speed and the efficiency of the collimation of the input light. The AOTF is powered by model N-2117 Sweep Oscillator (Interactive Radiation Inc., Northvale, N.J.). The tunable output of the sweep oscillator is selectable in the range 34–63 MHz by analog input voltages between 0–6.5 V. In this example the sweep oscillator is controlled by a model 59501B Isolated DAC/Power Supply Programmer (Hewlett-Packard, Palo Alto, Calif.) and an F34 Function Generator (Interstate Electronics Corp.). The base wavelength is selected through an HPIB bus interface accessed from an HP 85A Microcomputer Controller (Hewlett-Packard, Palo Alto, Calif.).

For detection PbS detectors(10×10 mm) was used at ambient temperature (Infrared Industries, Inc.). The optical data was manipulated for composition analysis by the HP 85A microcomputer.

Figure 7A:
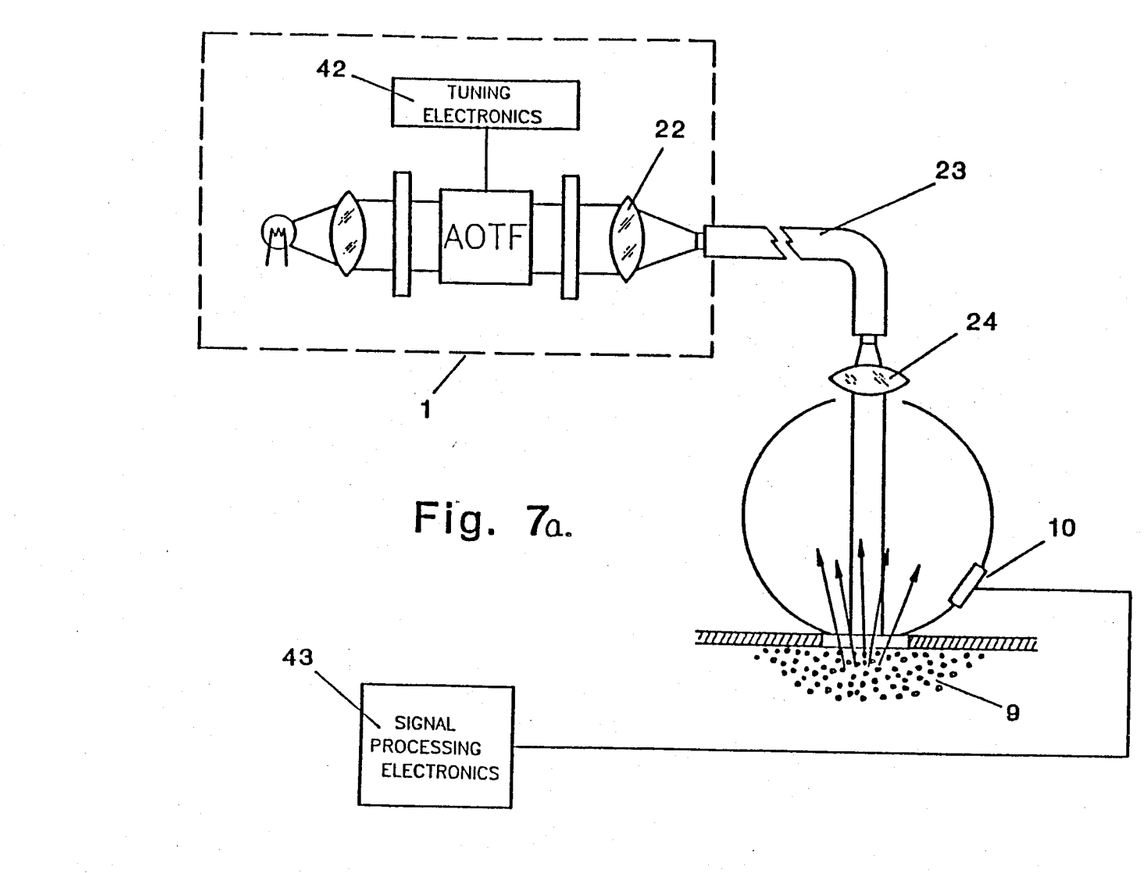
FIG. 7a. Fiber optic transmission of modulated light to the site of the measurement.

In another specific example of the preferred embodiment on FIG. 7a. the optical head was separated from the main instrument body by several feet. The instrument housing 41 contained a light source, the AOTF, the polarizers and related electronics 42, with the additional focusing lens 22 (f=25 mm aspheric lens, Melles Griot, Irvine, Calif.) and fiber optics 23. The modulated light of the selected wavelength is coupled by focusing lens 22 into fiber optic cable 23, capable of carrying the near-infrared radiation to a remote test point, the maximum distance being determined by the attenuation per distance of the fiber. At the remote location in this example, at the site of the chemical composition measurement for process control, light irradiates sample 9 directly or as on FIG. 7. through collimating lens 24. In the case of solid samples the reflected light is collected by an integrating sphere, onto detector 10. The signal is fed into signal electronic processing unit 43.

Figure 7B:
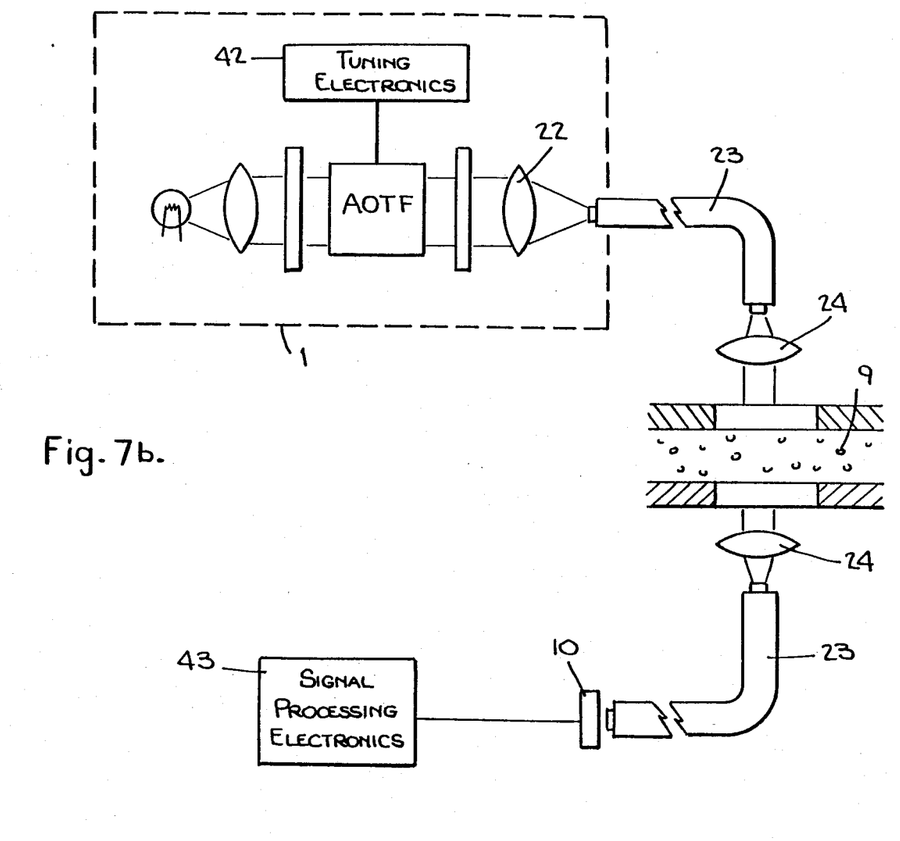

FIG. 7b differs from FIG. 7a, by position of a fiber optic coupling between the sample 9 and the detector 10.

Figure 8:
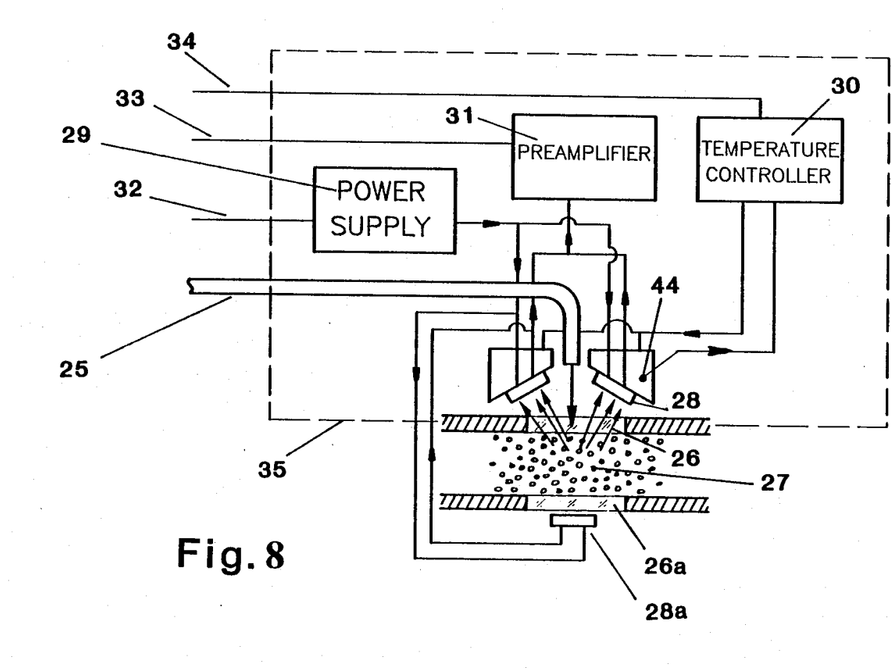
FIG. 8. Block diagram of remote optical head utilizing fiber optic illumination.

In a further specific example the block diagram of the remote head of the preferred embodiment is shown on FIG. 8. The remote head contains the illuminating fiber optics 25 here shown without any further collimation or refocusing, and without collection optics. The reflection detectors 28 are mounted on temperature controlled blocks, thermostatted by temperature regulator circuit 30 powered through supply connection 34. Thermistor 44 provides the control signal for the regulator circuit 30. In this example detectors are PbS detectors biased to about 200 V DC by regulated power supply 29, powered by line voltage 32, or Ge detectors without further thermostatting. In yet another example Si or Ge detector 28a. is placed on the other side of the sample layer 27, for transmittance measurement. The sample is illuminated through optical window 26, and the light is measured in this latter example through optical window 26a. The small signal from the detectors is amplified by preamplifier 31 and the amplified signal is transmitted through signal line 33 to the main instrument electronics. The simple optical head arrangement makes it possible to couple more than one remote head to one central instrument unit with the help of optical and electronic multiplexing for multipoint process analytical applications.

In any of the above examples all tuning schemes of FIGS. 3. and 4. can be used. In order to minimize the error of the analysis the timing of the wavelength change (base wavelength change) does not have to be equal.

What we claim is:

1. An apparatus for providing rapid random wavelength access for optical analysis of a sample comprising,
   (a) a light source,
   (b) an acousto-optic tunable filter positioned to accept light from the light source and provide emerging tuned output beams,
   (c) means to select a predetermined number of tuned beams from the acousto-optic tunable filter,
   (d) means to direct said predetermined number of selected tuned output beams onto the sample to be analyzed,
   (e) means to collect radiation that is reflected back to transmitted through said sample,
   (f) means for detecting and amplifying the reflected or transmitted radiation,
   (g) electronic tunable oscillator means connected to said acousto-optic tunable filter,
   (h) electronic means providing timing and logic for wavelength selection via said electronic tunable oscillator means, and
   (i) means for generating a predetermined periodic signal, said electronic means providing timing and logic for wavelength selection including means for generating a non-periodic signal, means for combining the periodic signal with the non periodic signal to provide a control input signal to the electronic tunable oscillator means to permit optical analyses of at least two discrete optical qualities of said sample.

2. The apparatus of claim 1 wherein the non periodic signal has two amplitudes such that the control input signal has more than two magnitudes corresponding to optical analysis wavelengths for measuring corresponding discrete qualities of a sample.

3. The apparatus as claimed in claim 1 including electronic signal generator means to deactivate the input to the acousto-optic tunable filter according to a predetermined reference frequency to provide modulation of light intensity for phase sensitive detection.

4. The apparatus of claim 1 further comprising optical focusing means and a fiber optic connection between said predetermined number of selected tuned output beams and said sample.

5. The apparatus of claim 1 further comprising a fiber optic coupling between said sample and said detection means.

6. The apparatus of claim 1 including square or sinewave generator means for generating said periodic signal.

7. The apparatus of claim 1 (including) wherein said electronic means providing timing and logic for wavelength selection includes a computer controlled digital-to-analog converter (and), said means for generating a predetermined periodic signal including a signal generator having a periodic signal output connected such that the output from the computer controlled digital-to-analog converter and the periodic signal output are combined to provide an input signal to the electronic tunable oscillator means.

8. The apparatus of claim 1 wherein the detection means is formed from at least one material selected from the group consisting of germanium, lead sulfide, lead selenide or silicon.

9. The apparatus of claim 1 including means to select predetermined beams according to their direction of propagation.

10. The apparatus of claim 1 further comprising a first polarizing means positioned to select at least one polarization direction from light emerging from said light source.

11. The apparatus of claim 10 further comprising a second polarizing means positioned to select one of the emerging tuned output beams.

12. A method of optical concentration analysis of a sample wherein
   (a) monochromatic light of different wavelengths is selected in rapid random succession with an acousto-optic tunable filter,
   (b) the successive wavelengths of monochromatic light are guided onto the sample,
   (c) the reflected or transmitted light intensity is measured,
   (d) the concentration of the sample is determined by substituting the intensities at different wavelengths or intensity differences at various wavelengths into a calibration equation, and
   (e) a periodic alternation is made between preselected wavelength pairs to permit optical analyses of at least two discrete optical qualities of said sample.

13. The method of claim 12 wherein the selection of wavelengths is such that each wavelength or wavelength pair is selected for different time intervals.

14. The method of claim 12 wherein the selection of wavelength is such that a base wavelength and a predetermined difference wavelength are selected, the base wavelength being tuned to a first predetermined value while the difference wavelength is maintained at a first constant magnitude to permit switching from the base wavelength by a wavelength magnitude corresponding to the predetermined difference wavelength.

15. The method of claim 14 wherein the base wavelength is tuned to a second predetermined value while maintaining the difference wavelength at said first constant magnitude.

16. The method of claim 14 wherein the base wavelength is tuned to a second predetermined value while the difference wavelength is changed to a second constant magnitude.

17. The method of claim 12 wherein the wavelength selection is accomplished by generating a predetermined periodic signal cooperable with a non-periodic signal and combining the periodic signal with the non-periodic signal.

* * * * *

UNITED STATES PATENT AND TRADEMARK OFFICE
CERTIFICATE OF CORRECTION

PATENT NO. : 4,883,963  Page 1 of 2

DATED : November 28, 1989

INVENTOR(S) : Gabor J. Kemeny; David L. Wetzel

It is certified that error appears in the above-identified patent and that said Letters Patent is hereby corrected as shown below:

At the cover page, in the OTHER PUBLICATIONS category, column 2, line 4, change "A perfume" to --Aperture--.

At column 5, line 27, delete "the".

At column 5, line 31, change "bur" to --but--.

At column 5, line 33, change "o" to --of--.

At column 5, line 47, after "crystal" add --.--.

At column 5, line 62, change "filtred" to --filtered--.

At column 6, line 49, change "wich" to --which--.

At column 10, line 9, change "to" (second occurrence) to --or--.

At column 10, line 48, delete "(including)".

UNITED STATES PATENT AND TRADEMARK OFFICE
CERTIFICATE OF CORRECTION

PATENT NO. : 4,883,963

DATED : November 28, 1989

INVENTOR(S) : Gabor J. Kemeny, et al

It is certified that error appears in the above-identified patent and that said Letters Patent is hereby corrected as shown below:

Column 10, line 51, delete "(and)".

Signed and Sealed this

Twenty-sixth Day of February, 1991

*Attest:*

HARRY F. MANBECK, JR.

*Attesting Officer*     *Commissioner of Patents and Trademarks*